United States Patent
Förtsch et al.

(10) Patent No.: US 8,918,154 B2
(45) Date of Patent: Dec. 23, 2014

(54) ENDOSCOPIC CAPSULE

(75) Inventors: Stefan Förtsch, Kunreuth (DE); Rainer Kuth, Höchstadt (DE); Karl-Heinz Maier, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 610 days.

(21) Appl. No.: 13/148,533

(22) PCT Filed: Feb. 15, 2010

(86) PCT No.: PCT/EP2010/051859
§ 371 (c)(1),
(2), (4) Date: Aug. 9, 2011

(87) PCT Pub. No.: WO2010/094652
PCT Pub. Date: Aug. 26, 2010

(65) Prior Publication Data
US 2011/0313266 A1 Dec. 22, 2011

(30) Foreign Application Priority Data

Feb. 17, 2009 (DE) .................. 10 2009 009 289
May 28, 2009 (DE) .................. 10 2009 023 038
Feb. 5, 2010 (DE) .................. 10 2010 006 970

(51) Int. Cl.
*A61B 5/1468* (2006.01)
*A61B 5/1473* (2006.01)
*A61B 5/05* (2006.01)
*A61B 5/07* (2006.01)
*A61B 1/04* (2006.01)
*A61B 5/00* (2006.01)
*A61B 5/053* (2006.01)

(52) U.S. Cl.
CPC .............. *A61B 5/6861* (2013.01); *A61B 5/073* (2013.01); *A61B 2560/0214* (2013.01); *A61B 1/041* (2013.01); *A61B 5/4839* (2013.01); *A61B 5/0538* (2013.01); *A61B 5/4238* (2013.01); *A61B 5/0031* (2013.01)
USPC ........................... 600/350; 600/380; 600/302

(58) Field of Classification Search
USPC ......... 600/309, 345, 348, 349, 350, 361, 380, 600/547, 302
See application file for complete search history.

(56) References Cited

U.S. PATENT DOCUMENTS 3,340,866 A 9/1967 Nöller
5,477,854 A * 12/1995 Essen-Moller ............... 600/350

(Continued)

FOREIGN PATENT DOCUMENTS

CN 2458626 11/2001
CN 101019764 11/2001

(Continued)

OTHER PUBLICATIONS

Highly Sophisticated Electrochemical Analysis System with an Integrated Microfluidic System Based on Electrowetting, Satoh et al., IEEE Sensors 2006, EXCO, Daegu, Korea, Oct. 22-25, 2006, pp. 1004-1007.

(Continued)

*Primary Examiner* — Navin Natnithithadha
(74) *Attorney, Agent, or Firm* — Schiff Hardin LLP

(57) ABSTRACT

An endoscopic capsule has a biocompatible capsule housing that contains at least one sensor device for acquiring medical data. The sensor is arranged on an outer surface of the housing, and has a first electrode produced of an acid-resistant noble metal, and a second electrode produced of silver. An electrical voltage is applied between the first and second electrodes, and a change in an electrical variable is measured between the first and second electrodes when ammonia is present. The endoscopic capsule allows screening of gastric acid and the tissue of the stomach lining for *Helicobacter pylori* in a manner that is gentle for the patient.

23 Claims, 1 Drawing Sheet

(56) References Cited

U.S. PATENT DOCUMENTS

| | | | |
|---|---|---|---|
| 5,507,289 | A | 4/1996 | Essen-Moller |
| 5,556,760 | A * | 9/1996 | Nakamura et al. ............... 435/12 |
| 6,419,809 | B1 * | 7/2002 | Suzuki et al. .................. 204/435 |
| 6,479,278 | B2 * | 11/2002 | Marshall .................... 435/287.9 |
| 2001/0012623 | A1 * | 8/2001 | Marshall ........................ 435/34 |
| 2003/0060702 | A1 | 3/2003 | Kuth et al. |
| 2004/0176664 | A1 * | 9/2004 | Iddan ............................ 600/160 |
| 2005/0043583 | A1 * | 2/2005 | Killmann et al. ............. 600/109 |
| 2005/0069932 | A1 * | 3/2005 | Arinaga et al. .................... 435/6 |
| 2005/0096502 | A1 * | 5/2005 | Khalili .......................... 600/106 |
| 2005/0148847 | A1 | 7/2005 | Uchiyama et al. |
| 2005/0192478 | A1 * | 9/2005 | Williams et al. ............. 600/160 |
| 2007/0021654 | A1 | 1/2007 | Preidel et al. |
| 2007/0138027 | A1 * | 6/2007 | Dinsmoor et al. ......... 205/787.5 |
| 2008/0200788 | A1 * | 8/2008 | Brister et al. ................. 600/345 |
| 2008/0255409 | A1 | 10/2008 | Graumann et al. |
| 2011/0092787 | A1 | 4/2011 | Bulitta et al. |

FOREIGN PATENT DOCUMENTS

| | | |
|---|---|---|
| CN | 1868396 | 11/2006 |
| JP | 01242034 | 9/1989 |
| JP | 07323034 | 12/1995 |
| JP | 09206095 A | 8/1997 |
| JP | 2007-071681 | 3/2007 |
| JP | 2007-155529 | 6/2007 |
| JP | 2008/026987 | 9/2008 |
| JP | 2009/028245 | 12/2009 |
| WO | WO99/30328 | 6/1999 |
| WO | 2006/045011 | 4/2006 |
| WO | WO 2007/020410 A1 | 2/2007 |
| WO | WO2007/020410 A1 | 2/2007 |

OTHER PUBLICATIONS

Effect of Helicobacter pylori infection on the kinetic profile of ammonia in gastric mucosa. A new diagnosis with an ammonia sensor. Kaoru, Journal of Osaka Medical College, 1999, vol. 58, Nr. 1, S. 51-61, englisches Abstract auf Science Links; Magazine; 1999.

"Helicobacter-Atemtest", Laborlexikon.de, Facharztwissen für alle, e-Journal für Labormedizin, http://www.laborlexikon.de/Lexikon/Infoframe/h/Helicobacter-Atemtest.htm.

"Helicobacter-Antigen im Stuhl", Laborlexikon.de, Facharztwissen für alle, e-Journal für Labormedizin, http://www.laborlexikon.de/Lexikon/Infoframe/h/Helicobacter-Antigen_Stuhl.htm.

"Menschen tragen seit 60.000 Jahren blinden Passagier im Bauch", Spiegel Online, 2007, http://www.spiegel.de/wissenschaft/mensch/0,1518,464986,00.html.

Vortrag von Jürgen Lorenzen, Olympus, "Erfahrungsaustausch zur Schadensprävention in der Endoskopie", 2. FKT-Fortbildungsveranstaltung 2008, Landesgruppe Hamburg am (2008).

Neumann et al., "Immediate detection of *Helicobacter* infection with a novel electrochemical system: Feasibility and comparison of diagnostic yield with immunohistochemistry, 13C urea breath test and *Helicobacter* urease test", Vortrag anlässlich der Digestive Disease Week in New Orleans, 1.-5. May 2010.

Foertsch et al., "Development of a new electrochemical device for rapid helicobacter pylori detection", Vortrag anlässlich der Digestive Disease Week in New Orleans, 1.-5. May 2010.

Petack, Olympus Deutschland GmbH, "Gerätetechnik Flexible Endoskope", (2008).

Ji et al., "The electrochemical oxidation of ammonia at boron-doped diamond electrodes exhibits analytically useful signals in aqueous solutions", Analyst, 2005, vol. 130, pp. 1345-1347, (2005).

* cited by examiner

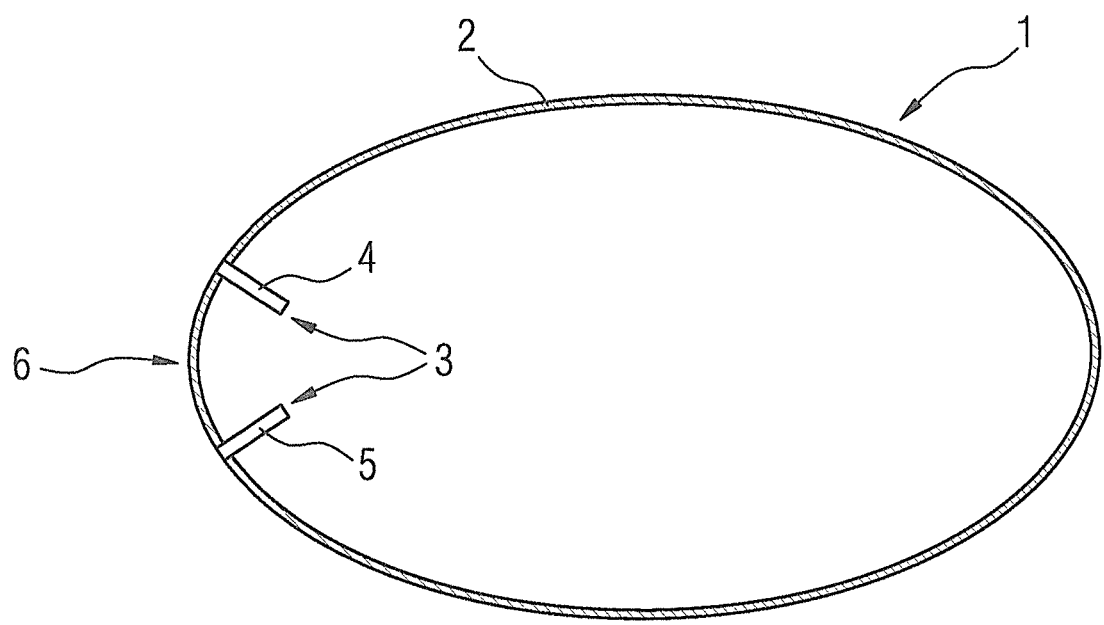

ENDOSCOPIC CAPSULE

BACKGROUND OF THE INVENTION

1. Field of the Invention

The invention relates to an endoscopic capsule with a biocompatible housing, in which at least one sensor apparatus for detecting medically relevant data is arranged.

2. Description of the Prior Art

A common cause for discomforts in the upper gastrointestinal tract is a bacterial affliction of the organs therein. By way of example, an affliction with *Helicobacter pylori* is held responsible for a vast range of gastric disorders that go are associated with an increased secretion of gastric acid. For example, these include type B gastritis, approximately 75% of gastric ulcers and almost all duodenal ulcers. Hence, examining the hollow organs of the gastrointestinal tract for bacteria populations, more particularly *Helicobacter pylori* populations, is an important component for diagnosing gastric disorders.

For example, *Helicobacter pylori* is detected using a breath test, in which a patient is administered C-13 masked urea. The C-13 masked $CO_2$, which is created when urea ($CO(NH_2)_2$) is split into ammonia ($NH_3$) and carbon dioxide ($CO_2$), is detected in the exhaled air. Other methods for detecting *Helicobacter pylori* are directed at typical blood values such as pepsinogen or gastrin. However, such methods are complex and only have limited reliability. A further test for *Helicobacter pylori* is the detection of the *Helicobacter pylori* antigen in fecal matter.

A further option for examining the stomach for a *Helicobacter pylori* population is provided by so-called gastroscopy. During such an examination, a gastroenterologist takes a tissue sample (biopsy specimen) from the mucosa of the stomach by means of a biopsy in order to examine, either immediately or at a later stage, whether there is an infection with *Helicobacter pylori*. A known examination method for the tissue sample is, for example, the *Helicobacter* urease test (HU test, abbreviated HUT). The biopsy specimen is placed into a test medium (measurement solution), which consists of a nutrient solution for this bacteria, urea, and an indicator (litmus). If *Helicobacter pylori* bacteria is contained in the sample, the bacteria splits the urea ($CO(NH_2)_2$) using urease into ammonia ($NH_3$) and carbon dioxide ($CO_2$). The ammonia then colors the indicator red. The test result is ready after a few minutes. The onset of color change from yellow to red cannot unambiguously be identified in inexpedient conditions.

An alternative to gastroscopy carried out using a flexible endoscope consists of using a so-called endoscopic capsule. Such an endoscopic capsule, which is also referred to as a capsule endoscope or endocapsule, is embodied as a passive endocapsule or a navigable endocapsule. A passive endoscopic capsule moves through the intestines of the patient as a result of peristalsis.

For example, a navigable endocapsule is known from patent DE 101 42 253 C1 and the corresponding patent application US 2003/0060702 A1, and therein it is referred to as an "Endoroboter" or "endo-robot". The endo-robot known from these publications can be navigated in a hollow organ (e.g. gastrointestinal tract) of a patient by means of a magnetic field, which is generated by an external (i.e. arranged outside of the patient) magnetic system (coil system). An integrated system for controlling the position, that includes a positional measurement of the endo-robot and automatic regulation of the magnetic field or the coil currents, can be used to detect changes automatically in the position of the endo-robot in the hollow organ of the patient and to compensate for these. Furthermore, the endo-robot can be navigated to desired regions of the hollow organ in a targeted fashion. It is for this reason that this type of capsule endoscopy is also referred to as magnetically guided capsule endoscopy (MGCE).

SUMMARY OF THE INVENTION

An object of the present invention is to provide an endoscopic capsule which allows an examination of the gastric acid and the tissue of the mucosa of the stomach for *Helicobacter pylori* that does not put much strain on a patient.

The endoscopic capsule according to the invention has a biocompatible housing, in which at least one sensor apparatus for detecting medically relevant data is arranged. According to the invention, on the outside of the housing, a sensor is arranged, wherein the sensor comprises a first electrode made of a noble metal, which cannot be attacked by acid (e.g. hydrochloric acid, phosphoric acid, sulfuric acid, gastric acid), and a second electrode made of silver. An electric voltage can be applied between the first electrode and the second electrode, and a change in an electric variable can be measured if ammonia is present between the first electrode and the second electrode.

In the endoscopic capsule according to the invention, ammonia ($NH_3$) can in a simple fashion be detected directly in the gastrointestinal tract of a patient during the examination, without taking a tissue sample. The endoscopic capsule according to the invention therefore allows an examination of the gastric acid and the tissue of the mucosa of the stomach for *Helicobacter pylori* that does not put much strain onto the patient.

In a preferred endoscopic capsule according to claim 2, the electric voltage between the first electrode and the second electrode equals zero. Thus no current flows between the first electrode and the second electrode. Advantageously, the potential is thereby measured (i.e. without a current) between the first electrode and the second electrode. Thus there hardly is ionic migration in the gastric acid.

In a further advantageous embodiment according to the invention, the electric voltage between the first electrode and the second electrode is an AC voltage with a variably predeterminable frequency spectrum. If gastric acid is exposed to direct current or a directed potential the ions migrate to the associated electrodes, i.e. the cations (e.g. ammonium $NH_4^+$) migrate to the cathode and the anions (e.g. chloride $Cl^-$) migrate to the anode. By applying a suitable AC voltage, the endoscopic capsule according to claim 3 reliably prevents complete charging of the first electrode (reference electrode) and complete charging of the second electrode (measurement electrode) because the migration speed of the ions in the gastric acid is almost zero if the frequency is sufficiently high.

When an AC voltage is applied, there is a cyclical change at the second electrode (measurement electrode), which, according to the invention, consists of silver (Ag), between destruction and buildup of the silver chloride (AgCl) layer. Both the destruction of the silver chloride layer and the buildup thereof can be measured by e.g. an impedance measurement and can be compared cyclically. The potential differences and phase differences that can be measured in the process are characteristic for the presence of urease activity, as a result of which presence of *Helicobacter pylori* can be deduced with a very high certainty.

In a further embodiment according to the invention, the frequency spectrum of the AC voltage is modulated. As a result, a higher AC voltage stability is obtained, which increases the measurement accuracy and reduces the measurement duration.

In another embodiment according to the invention, the electric voltage between the first electrode and the second electrode is a DC voltage, which can be applied for a predeterminable period of time. The predeterminable period of time during which an electric voltage can be applied by the user between the first electrode and the second electrode may lie between zero seconds and continuously, wherein the electric voltage selected by the user may be zero volts or higher. In the case of a period of time of zero seconds or a voltage of zero volts, this is a passive measurement. In the case of values deviating from these, this is an active measurement.

In other embodiments of the endoscopic capsule according to the invention, e.g. potentials, electric currents or electric resistances or the changes therein or variables (e.g. electric conductivity) derived from the electric variables or changes therein can be measured as electric variables.

The second electrode (measurement electrode), which consists of silver (Ag) in the case of the endoscopic capsule according to the invention, must be etched by hydrochloric acid (HCl). This may (but this is not necessary) already occur for the first time before the endoscopic capsule or the second electrode is supplied. However, it is also possible for the users themselves to undertake the initial HCl etching or apply an appropriate silver chloride layer by means of a suitable electrolytic method. After HCl etching or after electrolytic deposition, the second electrode has a silver chloride (AgCl) coating on its surface and is therefore activated for the measurement to detect *Helicobacter pylori*.

Using the endoscopic capsule according to claim 1, ammonia ($NH_3$) can in a simple fashion be detected directly in the gastrointestinal tract of the patient during the examination, without taking a tissue sample.

The endoscopic capsule according to the invention allows simple open or closed loop control of the sensor or its first electrode (reference electrode) and/or its second electrode (measurement electrode) e.g. by means of a baseline correction. Furthermore, a reproducible regeneration of the sensor, more particularly the second electrode, is possible after each examination.

If the measures outlined above are taken, the second electrode is not completely charged, and so a regeneration of the second electrode only becomes necessary after a multiplicity of examinations.

Moreover, the sensitivity of the sensor and/or its first and/or second electrode can be set in a simple fashion in the endoscopic capsule according to the invention. The sensitivity can be set before and during the examination in respect of *Helicobacter pylori*.

Platinum (Pt) and gold (Au) can be used as noble metals that are not attacked by acid and therefore are suitable for the first electrode (reference electrode).

After the patient has swallowed the endoscopic capsule according to the invention, the sensor detects ammonia ($NH_3$) present in the gastric acid and in the tissue of the mucosa of the stomach on the stomach inner wall. This is used to detect affliction of the tissue (mucosa of the stomach) with *Helicobacter pylori* in a patient-friendly fashion by detecting ammonia ($NH_3$). This takes place without a biopsy and therefore puts much less strain on the patient.

The detection of ammonia is a very strong indication for the presence of *Helicobacter pylori* because ammonia is generated by the *Helicobacter pylori* bacteria by splitting urea using urease in order to protect itself from the acidic environment of the gastrointestinal tract, more particularly the high acid concentration in the stomach.

As noted above, second electrode (measurement electrode), which consists of silver (Ag) in the endoscopic capsule according to the invention, must be etched by hydrochloric acid (HCl). After the HCl etching, the second electrode has a silver chloride (AgCl) coating on its surface and is therefore activated for the measurement to detect *Helicobacter pylori*. The activation of the second electrode is based on the following chemical reaction:

$$Ag + HCl \rightarrow AgCl + H^+ + e^-$$

Since ammonia ($NH_3$) under normal circumstances does not occur, or only occurs in very low concentrations in a hollow organ of the gastrointestinal tract, such as the stomach, as a result of the following neutralization reaction (forming an ammonium cation by protonation of ammonia)

$$NH_3 + H^+ \leftrightarrows NH_4^+$$

the detection thereof is a very strong indication for the presence of *Helicobacter pylori*. The proton ($H^+$, hydrogen nucleus) is a component of the gastric acid.

The corresponding chemical reaction for detecting *Helicobacter pylori* is:

$$AgCl + 2NH_3 \rightarrow [Ag(NH_3)_2]^+ + Cl^-$$

The AgCl salt (silver chloride) is split into the silver-diammine complex $[Ag(NH_3)_2]^+$ and chloride $Cl^-$ by ammonia. $[Ag(NH_3)_2]^+$ as a cation is very soluble in water and absorbed by the gastric acid. As per advantageous embodiments of the endoscopic capsule according to the invention, there is between the first electrode (reference electrode) and second electrode (measurement electrode) either an electric voltage of zero or an electric AC voltage with a variably predeterminable frequency spectrum. Alternatively, a DC voltage can be applied between the first electrode and the second electrode for a predeterminable period of time. In all cases, there is barely any ion migration in the gastric acid (migration speed of the cations and anions is approximately zero).

The electric variable (potential, electric current, electric resistance) measured between the first electrode (reference electrode) and second electrode (measurement electrode) is recorded, displayed, and—if desired—transmitted to evaluation electronics. As a result of an (automated) comparison between the measured value and predetermined values, a possible affliction of the mucosa of the stomach with *Helicobacter pylori* can be reliably indicated.

The sensor of the endoscopic capsule can be regenerated in vivo after each individual measurement and afterwards is available for further measurements. After the endoscopic capsule has been excreted, it can be disposed of or recycled. It is expedient to clean the endoscopic capsule with its sensors with an ammoniacal rinsing solution (ammoniacal disinfectant) before feeding to the sterilization process, in order to remove possible remains of AgCl. The endoscopic capsule according to the invention can thus once again be used for detecting *Helicobacter pylori* after a possible necessary recalibration of the sensor. For example, the sensor can be calibrated by a dose of synthetic ammonia.

The endoscopic capsule according to the invention allows an examination, which only puts little strain on the patient, of the mucosa of the stomach in respect of *Helicobacter pylori*, wherein tissue samples are only taken if the presence of *Helicobacter pylori* is suspected. The endoscopic capsule can take tissue samples if it has a biopsy apparatus.

In addition to the sensor provided according to the invention, a therapeutic device for administering therapeutic means is arranged in the housing in an advantageous embodiment of the endoscopic capsule.

In further advantageous exemplary embodiments of the endoscopic capsule according to the invention, at least one data storage medium and/or at least one data transmission apparatus are arranged in the housing.

Furthermore, evaluation electronics are provided in the housing as per one preferred embodiment of the endoscopic capsule. The values established by the evaluation electronics can be stored in the data storage medium and/or transmitted directly to a reception apparatus situated outside of the human or animal body.

The energy required for the evaluation, data storage, and/or data transmission is provided by an energy store in a particularly preferred embodiment of the endoscopic capsule, which energy store is preferably embodied as a rechargeable energy store (rechargeable battery, capacitor).

The once or repeated charging of the energy store can for example be brought about inductively or via the two electrodes (reference electrode, measurement electrode) of the sensor arranged on the external surface of the housing. If the energy store is equipped with at least one solar cell and if the housing of the endoscopic capsule is transparent, at least in the vicinity of the solar cell, then the energy store can be charged for the subsequent examination, for example by irradiating the endoscopic capsule with laser light in the transparent region of the housing.

As an alternative to an energy store that was charged prior to the examination, the endoscopic capsule can also during an examination be supplied continuously with the required energy by induction. To this end, the patient must merely be situated in the vicinity of an alternating magnetic field.

Within the scope of the invention, the endoscopic capsule may be embodied as a passive endoscopic capsule or as a navigable endoscopic capsule ("endo-robot"). A passive endoscopic capsule moves through the intestines of the patient as a result of peristalsis, whereas a navigable endoscopic capsule has at least one magnetic element arranged in its housing for the purpose of navigation by means of a magnetic field that can be generated by an external magnetic system.

In order to register all regions of the stomach wall of a patient after the latter has taken a passive endoscopic capsule, the patient assumes different positions during the examination in order thereby to move the endoscopic capsule into various regions of the stomach of said patient. Advantageously, the positions that the patient must assume for this purpose are output in a standardized sequence by a patient monitoring system and a positive test result (detection of ammonia) is linked to the associated position of the patient. To this end, the respective positions of the patient are preferably recorded by an external video-camera system with appropriate image-processing software. In order to improve the registration of the position of the patient, the latter can for example wear a belt provided with a marking that, for example, reflects if irradiated by infrared light and can therefore be detected by the external video-camera system in an improved fashion.

If the patient is administered a navigable endoscopic capsule, this endoscopic capsule is navigated in the stomach of the patient by means of a magnetic field, which is generated by an external (i.e. arranged outside of the patient) magnetic system (coil system). As a result of the alternating magnetic field generated by the coil system, the endoscopic capsule can during an examination moreover be supplied continuously with the required energy by induction.

If a reuse of the endoscopic capsule, as described in DE 10 2007 017 267 A1, is desired, the patient is provided with an induction detector, by means of which said patient can register the position of the endoscopic capsule within the gastrointestinal tract or in the toilet. After the examination has been completed, the patient can send the excreted endoscopic capsule and the induction detector to a service provider for reconditioning.

BRIEF DESCRIPTION OF THE DRAWINGS

The single FIGURE schematically illustrates an endo-robot in accordance with the invention.

DESCRIPTION OF THE PREFERRED EMBODIMENTS

The invention and further advantageous embodiments are explained in more detail below in the drawing on the basis of a schematically illustrated exemplary embodiment; however, the invention is not restricted to the explained exemplary embodiment.

The only FIGURE shows an endoscopic capsule 1, as known from e.g. DE 101 42 253 C1, mentioned at the outset, and the corresponding US 2003/0060702 A1, the contents of which are incorporated herein by reference.

The endoscopic capsule 1 (capsule endoscope, endo-robot) has an ellipsoidal housing 2, i.e. it has respectively one capsule tip at both ends. At least one sensor apparatus for registering medically relevant data is arranged in the housing 2, which is formed of biocompatible material.

According to the invention, a sensor 3, which is part of the sensor apparatus, is arranged on the external surface of the housing 2. The parts of the sensor apparatus arranged within the housing 2 are known from e.g. DE 101 42 253 C1 and are therefore not illustrated in the drawing.

The sensor 3 has a first electrode 4 (reference electrode) made of a noble metal, which cannot be attacked by hydrochloric acid, and a second electrode 5 (measurement electrode) made of silver (Ag). The second electrode 5 has a silver chloride layer (AgCl layer) on its surface and is therefore activated for the measurement to detect *Helicobacter pylori*.

In the illustrated exemplary embodiment of the endoscopic capsule 1, the first electrode 4 and the second electrode 5 are arranged in the region of a capsule tip 6 at a constant distance from one another.

An electric voltage can be applied between the first electrode 4 and the second electrode 5, as a result of which a change in an electric variable, e.g. potential, electric current, or electric resistance, can be measured if ammonia is present between the first electrode 4 and the second electrode 5.

Platinum (Pt) and gold (Au) can be used as noble metals that are not attacked by hydrochloric acid and therefore are suitable for the first electrode 5.

Alternatively or additionally, other arrangements of the sensor 3 and/or the first electrode 4 and/or the second electrode 5 are also possible within the scope of the invention. Thus, e.g. the first electrode 4 can be arranged at one capsule tip and the second electrode 5 at the other capsule tip. As a further variant, an arrangement of both electrodes 4 and 5 in the circumferential region of the housing 2 of the endoscopic capsule can also be realized.

Although modifications and changes may be suggested by those skilled in the art, it is the intention of the inventors to embody within the patent warranted heron all changes and

We claim as our invention:

1. An endoscopic capsule comprising:
   a biocompatible capsule housing having a size and shape for movement through the gastrointestinal tract of a subject;
   a sensor apparatus inside said housing that detects medical information;
   a sensor located at an exterior of said housing, that is exposed to an interior of the gastrointestinal tract, and communicating with said sensor apparatus, said sensor comprising a first electrode made of a noble metal, which cannot be attacked by acid; and a second electrode made of silver with a silver chloride layer that is exposed to said interior;
   said sensor apparatus comprising a voltage source connected between said first electrode and said second electrode that produces an electric voltage between said first electrode and said second electrode with said first electrode operated as a reference electrode and said second electrode operated as a measurement electrode; and
   said sensor apparatus comprising a detector that detects a change in an electrical variable between said first electrode and said second electrode when ammonia is present in said interior between said first electrode and said second electrode, by said silver chloride layer participating in a chemical reaction with said ammonia.

2. An endoscopic capsule diagnostic device as claimed in claim 1 wherein said voltage source produces an electric voltage between said first electrode and said second electrode of zero.

3. An endoscopic capsule diagnostic device as claimed in claim 1 wherein said voltage source produces said electric voltage source as an AC voltage with a variable frequency spectrum.

4. An endoscopic capsule diagnostic device as claimed in claim 1 wherein said voltage source produces said electric voltage as a DC voltage for a predetermined period of time.

5. An endoscopic capsule diagnostic device as claimed in claim 1 wherein said detector measures electrical potential as said electrical variable.

6. An endoscopic capsule diagnostic device as claimed in claim 1 wherein said detector measures electrical current as said electrical variable.

7. An endoscopic capsule diagnostic device as claimed in claim 1 wherein said detector measures electrical resistance as said electrical variable.

8. An endoscopic capsule diagnostic device as claimed in claim 1 wherein said first electrode is made of a noble metal selected from the group consisting of platinum and gold.

9. An endoscopic capsule diagnostic device as claimed in claim 1 wherein at least one of said first electrode and said second electrode is configured to be replaceable.

10. An endoscopic capsule diagnostic device as claimed in claim 1 wherein said second electrode is regenerable.

11. An endoscopic capsule as claimed in claim 1 comprising, in said capsule housing, a therapeutic device that administers therapy via said capsule housing.

12. An endoscopic capsule as claimed in claim 1 comprising, in said housing, at least one magnetic element that navigates said capsule housing by interaction with a magnetic field produced by an extracorporeal magnet system.

13. An endoscopic capsule as claimed in claim 1 comprising, in said housing, a data storage medium in which at least sensor data produced by said sensor are stored.

14. An endoscopic capsule as claimed in claim 1 comprising, in said housing, evaluation electronics that evaluates sensor data produced by said sensor.

15. An endoscopic capsule as claimed in claim 1 comprising, in said capsule housing, at least one data transmission device configured to transmit data to a location external of said housing.

16. An endoscopic capsule as claimed in claim 1 comprising, in said housing, an energy storage unit that forms said voltage source.

17. An endoscopic capsule diagnostic device as claimed in claim 1 wherein said voltage source generates said electrical voltage as an AC sinusoidal voltage.

18. An endoscopic capsule diagnostic device as claimed in claim 1 wherein said voltage source generates said electrical voltage as an AC triangular voltage.

19. An endoscopic capsule diagnostic device as claimed in claim 1 wherein said voltage source generates said electrical voltage as an AC sawtooth voltage.

20. An endoscopic capsule diagnostic device as claimed in claim 1 wherein said voltage source generates said electrical voltage as an AC voltage representing a noise spectrum.

21. An endoscopic capsule diagnostic device as claimed in claim 1 wherein said voltage source generates said electrical voltage as an AC voltage having a variable frequency spectrum comprised of at least two pulses with respectively different shapes.

22. An endoscopic capsule diagnostic device as claimed in claim 1 wherein said voltage source generates said electrical voltage as an AC voltage with a variable frequency spectrum comprised of components having respectively different bandwidths.

23. An endoscopic capsule diagnostic device as claimed in claim 1 wherein said voltage source generates said electrical voltage as a modulated AC voltage having a variable frequency spectrum.

* * * * *